(12) United States Patent
Lovell et al.

(10) Patent No.: US 8,900,137 B1
(45) Date of Patent: Dec. 2, 2014

(54) CERVICAL RETRACTOR

(75) Inventors: Nathan Lovell, Oceanside, CA (US);
Michael Serra, San Diego, CA (US);
Michael Brotman, San Diego, CA (US);
Andrew Wolf, Del Mar, CA (US);
Kenneth Rich, Raleigh, NC (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/457,484

(22) Filed: Apr. 26, 2012

Related U.S. Application Data

(60) Provisional application No. 61/479,307, filed on Apr. 26, 2011.

(51) Int. Cl.
*A61B 17/02* (2006.01)

(52) U.S. Cl.
USPC ........... 600/232; 600/210; 600/213; 600/215; 600/219

(58) Field of Classification Search
USPC ......... 600/201, 204, 205, 210, 213–219, 221, 600/222, 227–234; 606/90, 105; 16/337, 16/321; 403/144
See application file for complete search history.

(56) References Cited

U.S. PATENT DOCUMENTS

| 1,223,812 A | 4/1917 | Listiak |
| 1,456,116 A | 5/1923 | Bessesen |
| 2,807,259 A | 9/1957 | Guerriero |
| 3,030,948 A | 4/1962 | Loeffler |
| 3,384,077 A | 5/1968 | Gauthier |
| 3,509,873 A | 5/1970 | Karlin |
| 3,522,799 A | 8/1970 | Gauthier |
| 3,635,435 A * | 1/1972 | Perison, Sr. .................. 248/549 |
| 3,724,449 A | 4/1973 | Gauthier |
| 3,749,088 A | 7/1973 | Kohlmann |
| 3,965,890 A | 6/1976 | Gauthier |
| 186,637 A | 1/1977 | Tanner |
| 4,024,859 A | 5/1977 | Slepyan |
| 4,116,232 A | 9/1978 | Rabban |
| 4,151,837 A | 5/1979 | Millard |
| 4,156,424 A | 5/1979 | Burgin |
| 4,165,746 A | 8/1979 | Burgin |
| 4,457,300 A | 7/1984 | Budde |
| 4,461,284 A | 7/1984 | Fackler |

(Continued)

FOREIGN PATENT DOCUMENTS

| CA | 1142826 | 3/1983 |
| CN | 201341901 | 11/2009 |

(Continued)

*Primary Examiner* — Michael T Schaper
*Assistant Examiner* — Tracy Kamikawa
(74) *Attorney, Agent, or Firm* — Jonathan Spangler; Rory Schermerhorn

(57) ABSTRACT

An anterior cervical retractor comprises a retractor body having a base arm and a moving arm and a pair of retractor blades having a side loading blade and a top loading blade. The base arm includes a first track and a side loading connector. The first track extends perpendicularly from a proximal end of the base arm and the first track includes an articulating arm post and a gear teeth. The moving arm is located opposite to the base arm and includes a first track receptacle and a top loading connector. The moving arm is advanced along the first track by means of a knob extending from the base arm. The side loading blade includes a first blade portion and a first connection post and the top loading blade includes a second blade portion and a second connection post.

16 Claims, 6 Drawing Sheets

(56) References Cited

U.S. PATENT DOCUMENTS

| | | |
|---|---|---|
| 4,686,972 A | 8/1987 | Kurland |
| 4,702,230 A | 10/1987 | Pelta |
| 4,747,394 A | 5/1988 | Watanabe |
| 4,747,395 A | 5/1988 | Brief |
| 4,817,587 A | 4/1989 | Janese |
| 4,829,985 A | 5/1989 | Couetil |
| 4,852,552 A | 8/1989 | Chaux |
| 4,881,525 A | 11/1989 | Williams |
| 4,934,352 A | 6/1990 | Sullivan |
| 5,052,373 A | 10/1991 | Michelson |
| 5,512,038 A | 4/1996 | O'Neal |
| D369,860 S | 5/1996 | Koros |
| 5,733,290 A | 3/1998 | McCue |
| 5,772,583 A | 6/1998 | Wright |
| 5,795,291 A * | 8/1998 | Koros et al. ............... 600/232 |
| 5,846,192 A | 12/1998 | Teixido |
| 5,846,193 A * | 12/1998 | Wright .......................... 600/215 |
| 5,865,730 A | 2/1999 | Fox |
| 5,882,298 A | 3/1999 | Sharratt |
| 5,893,831 A | 4/1999 | Koros |
| 5,902,233 A | 5/1999 | Farley |
| 5,931,777 A | 8/1999 | Sava |
| 5,944,658 A | 8/1999 | Koros |
| 5,967,974 A | 10/1999 | Nicholas |
| 5,984,865 A | 11/1999 | Farley |
| 5,993,385 A | 11/1999 | Johnston |
| 6,042,540 A * | 3/2000 | Johnston et al. ............... 600/213 |
| 6,042,542 A | 3/2000 | Koros |
| 6,200,263 B1 | 3/2001 | Person |
| 6,206,826 B1 | 3/2001 | Mathews |
| 6,206,828 B1 | 3/2001 | Wright |
| 6,213,941 B1 | 4/2001 | Benetti |
| 6,224,545 B1 | 5/2001 | Cocchia |
| 6,234,961 B1 | 5/2001 | Gray |
| 6,241,729 B1 | 6/2001 | Estes |
| 6,264,396 B1 | 7/2001 | Dobrovolny |
| 6,296,609 B1 | 10/2001 | Brau |
| 6,322,500 B1 | 11/2001 | Sikora |
| 6,340,345 B1 | 1/2002 | Lees |
| 6,416,465 B2 | 7/2002 | Brau |
| 6,506,151 B2 | 1/2003 | Estes |
| 6,524,238 B2 | 2/2003 | Velikaris |
| 6,602,190 B2 | 8/2003 | Dobrovolny |
| 6,648,818 B2 | 11/2003 | Cartier |
| 6,685,632 B1 | 2/2004 | Hu |
| 6,692,434 B2 | 2/2004 | Ritland |
| 6,733,444 B2 | 5/2004 | Phillips |
| 6,860,850 B2 | 3/2005 | Phillips |
| 6,887,197 B2 | 5/2005 | Phillips |
| 6,887,198 B2 | 5/2005 | Phillips |
| 6,929,606 B2 | 8/2005 | Ritland |
| 6,951,538 B2 | 10/2005 | Ritland |
| 7,001,333 B2 | 2/2006 | Hamel |
| 7,014,609 B2 | 3/2006 | Cartier |
| 7,056,287 B2 | 6/2006 | Taylor |
| 7,108,698 B2 | 9/2006 | Robbins |
| 7,147,599 B2 | 12/2006 | Phillips |
| 7,166,073 B2 | 1/2007 | Ritland |
| 7,182,729 B2 | 2/2007 | Abdelgany |
| 7,182,731 B2 | 2/2007 | Nguyen |
| 7,214,186 B2 | 5/2007 | Ritland |
| 7,235,048 B2 | 6/2007 | Rein |
| 7,294,104 B2 | 11/2007 | Person |
| 7,374,534 B2 | 5/2008 | Dalton |
| 7,396,328 B2 | 7/2008 | Penenberg |
| 7,455,639 B2 | 11/2008 | Ritland |
| 7,473,223 B2 | 1/2009 | Fetzer |
| 7,537,565 B2 | 5/2009 | Bass |
| 7,569,014 B2 | 8/2009 | Bass |
| 7,588,537 B2 | 9/2009 | Bass |
| 7,654,954 B1 | 2/2010 | Phillips |
| 7,722,618 B2 | 5/2010 | Estes |
| 7,744,530 B2 | 6/2010 | Person |
| 7,753,844 B2 | 7/2010 | Sharratt |
| 7,758,501 B2 | 7/2010 | Frasier |
| 7,850,608 B2 | 12/2010 | Hamada |
| 7,909,829 B2 | 3/2011 | Patel |
| 7,909,848 B2 | 3/2011 | Patel |
| 7,927,337 B2 | 4/2011 | Keller |
| 7,931,589 B2 | 4/2011 | Cohen |
| 7,935,053 B2 | 5/2011 | Karpowicz |
| 7,946,982 B2 | 5/2011 | Hamada |
| 7,959,564 B2 | 6/2011 | Ritland |
| 7,981,031 B2 | 7/2011 | Frasier |
| 8,062,217 B2 | 11/2011 | Boucher |
| 8,066,710 B2 | 11/2011 | Estes |
| 8,636,655 B1 | 1/2014 | Childs |
| 2005/0192486 A1 | 9/2005 | Hamel |
| 2005/0240081 A1 | 10/2005 | Eliachar |
| 2006/0183978 A1 | 8/2006 | Howard |
| 2006/0206009 A1 | 9/2006 | Von Wald |
| 2007/0038033 A1 | 2/2007 | Jones |
| 2007/0073112 A1 | 3/2007 | Holmes |
| 2007/0083086 A1 | 4/2007 | LeVahn |
| 2007/0129608 A1 | 6/2007 | Sandhu |
| 2007/0208228 A1 | 9/2007 | Pavento |
| 2007/0238932 A1 | 10/2007 | Jones |
| 2008/0071145 A1 | 3/2008 | Bjork |
| 2008/0114208 A1 | 5/2008 | Hutton |
| 2008/0146881 A1 | 6/2008 | Alimi |
| 2008/0249372 A1 | 10/2008 | Reglos |
| 2009/0012370 A1 | 1/2009 | Gutierrez |
| 2009/0012527 A1 | 1/2009 | Mignucci |
| 2009/0076333 A1 | 3/2009 | Bjork |
| 2009/0076516 A1 | 3/2009 | Lowry |
| 2009/0105547 A1 | 4/2009 | Vayser |
| 2009/0124861 A1 | 5/2009 | Fetzer |
| 2009/0227845 A1 | 9/2009 | Lo |
| 2010/0081885 A1 | 4/2010 | Wing |
| 2010/0113885 A1 | 5/2010 | Mcbride |
| 2010/0217089 A1 | 8/2010 | Farley |
| 2010/0298647 A1 | 11/2010 | Black |
| 2010/0298648 A1 | 11/2010 | Gray |
| 2010/0312068 A1 | 12/2010 | Dalton |
| 2011/0004067 A1 | 1/2011 | Marchek |
| 2011/0034781 A1 | 2/2011 | Loftus |
| 2011/0130793 A1 | 6/2011 | Woolley |
| 2011/0137130 A1 | 6/2011 | Thalgott |
| 2011/0144450 A1 | 6/2011 | Paolitto |
| 2011/0172494 A1 | 7/2011 | Bass |
| 2011/0172663 A1 * | 7/2011 | Mullaney .................... 606/59 |
| 2011/0201897 A1 | 8/2011 | Bertagnoli |
| 2011/0208008 A1 | 8/2011 | Michaeli |
| 2011/0224497 A1 | 9/2011 | Weiman |
| 2011/0245836 A1 | 10/2011 | Hamada |
| 2011/0257487 A1 | 10/2011 | Thalgott |
| 2011/0301423 A1 | 12/2011 | Koros |
| 2012/0083662 A1 | 4/2012 | Hamada |
| 2012/0130180 A1 | 5/2012 | Pell |
| 2012/0172670 A1 | 7/2012 | Hamada |
| 2012/0197300 A1 | 8/2012 | Loftus |
| 2012/0245432 A1 | 9/2012 | Karpowicz |
| 2012/0265021 A1 | 10/2012 | Nottmeier |
| 2012/0330106 A1 | 12/2012 | Wright |
| 2013/0046147 A1 | 2/2013 | Nichter |
| 2013/0123581 A1 | 5/2013 | Fritzinger |
| 2013/0158359 A1 | 6/2013 | Predick |
| 2013/0245383 A1 | 9/2013 | Friedrich |
| 2013/0261401 A1 | 10/2013 | Hawkins |
| 2013/0261402 A1 | 10/2013 | Hawkins |
| 2013/0303859 A1 | 11/2013 | Nowak |
| 2013/0345520 A1 | 12/2013 | Hamada |
| 2014/0024900 A1 | 1/2014 | Capote |
| 2014/0066718 A1 | 3/2014 | Fiechter |
| 2014/0066941 A1 | 3/2014 | Mignucci |

FOREIGN PATENT DOCUMENTS

| | | |
|---|---|---|
| CN | 201537102 | 8/2010 |
| DE | 29722605 | 2/1998 |
| EP | 1949860 | 3/2010 |
| EP | 2394584 | 12/2011 |
| FR | 2788958 | 8/2000 |
| GB | 1520832 | 8/1978 |

(56) References Cited

FOREIGN PATENT DOCUMENTS

| | | |
|---|---|---|
| JP | 10277043 | 10/1998 |
| WO | WO2004037070 | 5/2004 |
| WO | WO2004047650 | 6/2004 |
| WO | WO2007002405 | 1/2007 |
| WO | WO2010057980 | 5/2010 |
| WO | WO2012005914 | 1/2012 |
| WO | WO2012040206 | 3/2012 |
| WO | WO2012093368 | 7/2012 |
| WO | WO2012125975 | 9/2012 |
| WO | WO2013000105 | 1/2013 |
| WO | WO2013033630 | 3/2013 |
| WO | WO2013052827 | 4/2013 |

* cited by examiner

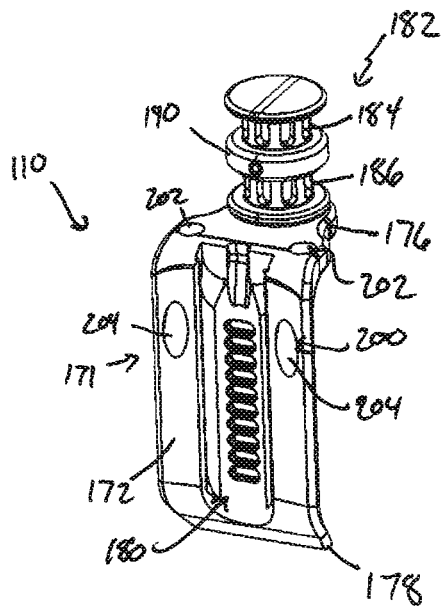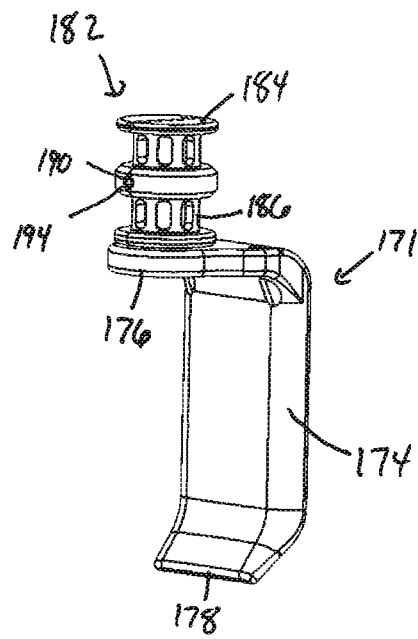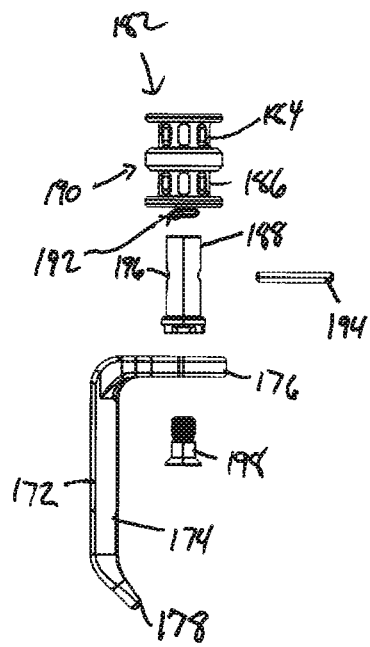
FIG. 4
FIG. 5
FIG. 6

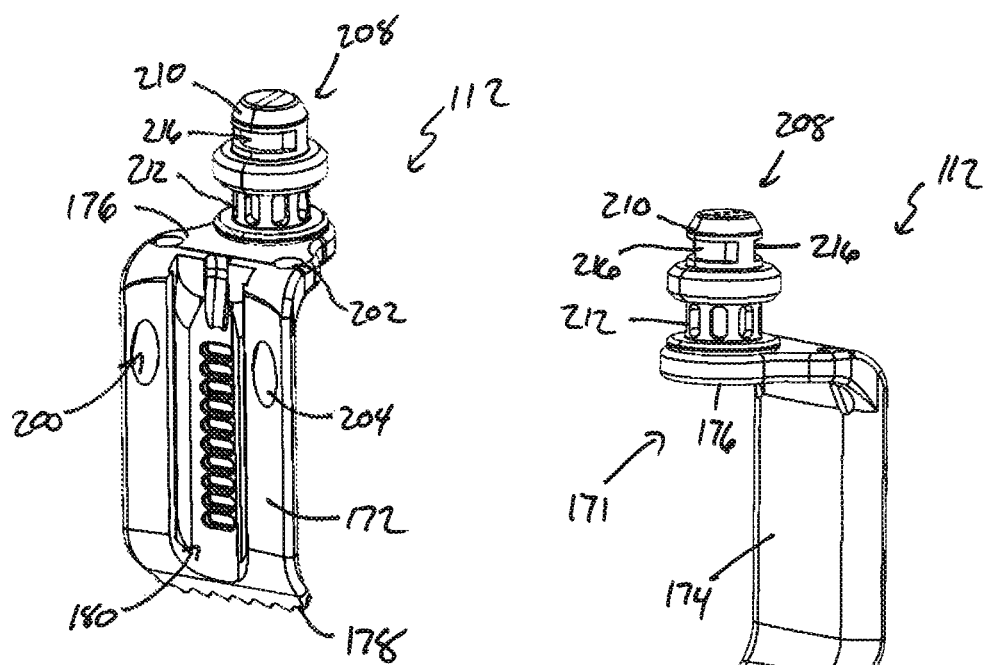
FIG. 7
FIG. 8
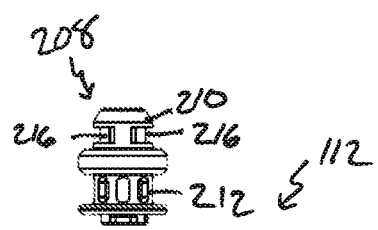
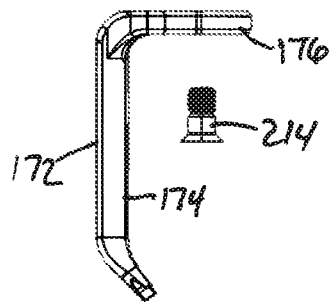
FIG. 9

CERVICAL RETRACTOR

CROSS REFERENCES TO RELATED APPLICATIONS

This application claims the benefit of priority under 35 U.S.C. 119(e) from U.S. Provisional Patent Application Ser. No. 61/479,307 filed on Apr. 26, 2011 the entire contents of which are each hereby expressly incorporated by reference into this disclosure as if set forth in its entirety herein.

TECHNICAL FIELD

This application describes surgical retractors useful for creating and maintaining an access corridor to the cervical spine.

BACKGROUND

Retractors are often used to assist surgeons during procedures. During spinal procedures for example, retractors are used to maintain an operative corridor free of body tissue from the exterior of the patient to the spinal target site. Procedures performed on the anterior cervical spine, for example, discectomy, fusion, disc replacement, etc. . . . are often performed with the aid of the retractor. These procedures are used to treat symptoms from cervical disc diseases or traumas such as cervical radiculopathy, disc herniations, fractures, and spinal instability.

In order to perform the anterior cervical discectomy, an incision incision is made through the neck and retractors are then used to gently separate and hold the neck muscles and soft tissues apart so that the surgeon can work on the front portion of the cervical spine. While there are a number of cervical retractors available for use, there remains room for improvement of cervical retractor offerings. For example, cervical retractors often use retractor blades that are fixed in a single position. These retractor blades are unable to adjust or move with the tissue as the tissue is retracted and pressure points can arise potentially causing unnecessary morbidity to the surrounding tissue. Other retractors used blades that are free to rotate relative to the retractor body. However, because these blades can rotate freely correctly aligning them during retractor deployment can also be a challenge. Additionally, retractors often have many parts that are free to move relative, which may be beneficial to achieve a desired retractor position, but which can lead to difficulty in handling the retractors outside of body.

The retractor, instruments, and methods described herein are aimed at addressing these and other challenges that currently exist.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

FIGS. 4-6 are front perspective, back perspective, and side exploded views of a side loading retractor blade, according to one example embodiment;

FIGS. 7-9 are front perspective, back perspective, and side exploded views of a top loading retractor blade, according to one example embodiment;

DETAILED DESCRIPTION OF A PREFERRED EMBODIMENT

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The anterior cervical retractor disclosed herein boasts a variety of inventive features and components that warrant patent protection, both individually and in combination.

Figure 1:
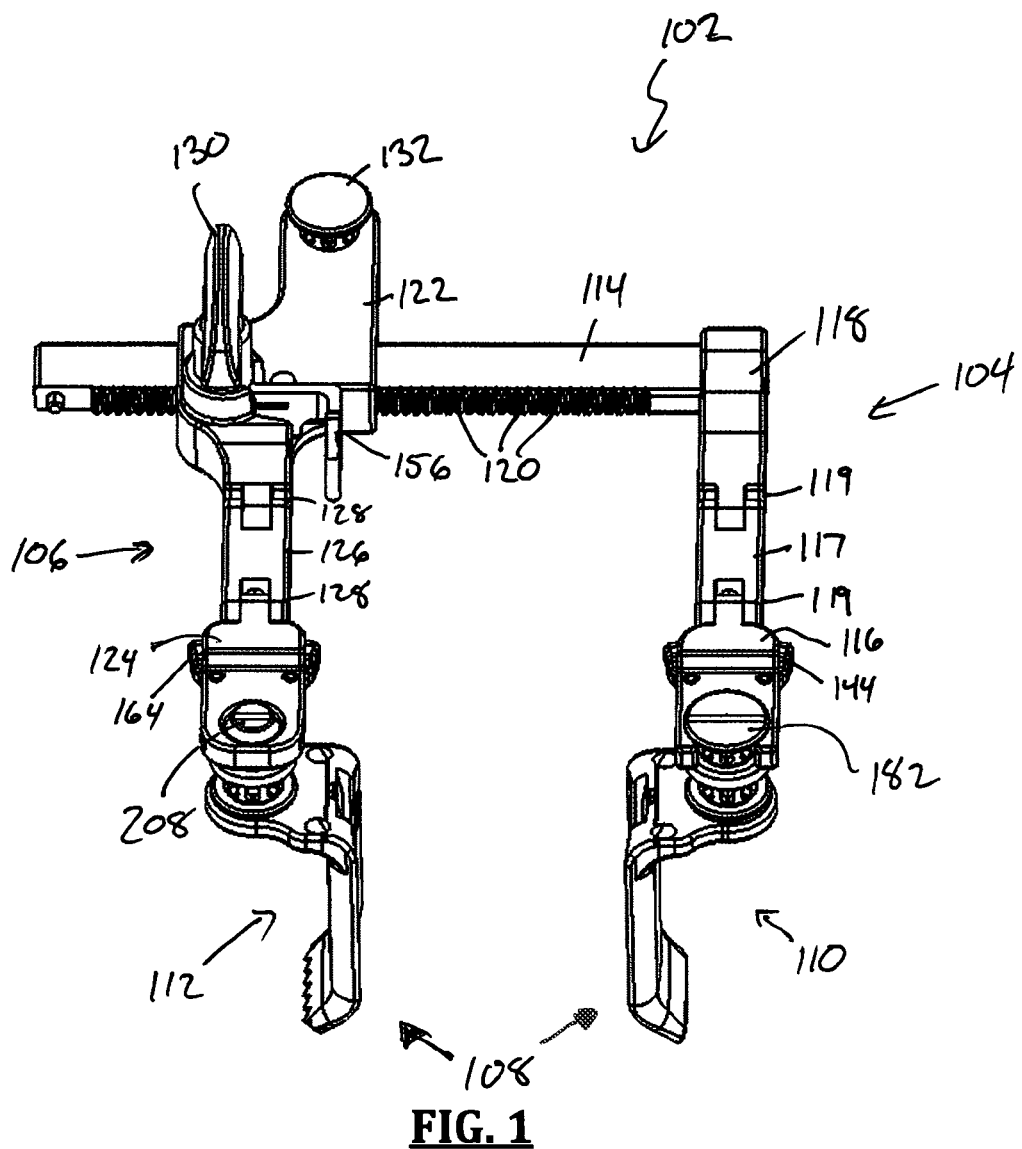
FIG. 1 is a perspective view of an anterior cervical retractor according to one example embodiment.

With reference to FIG. 1, a cervical retractor 102 according to one example embodiment is depicted. The cervical retractor 2 is well suited for creating an operative corridor to a cervical spine target site, particularly for a single level procedure (e.g. discectomy, fusion, disc replacement, etc. . . . ). The cervical retractor 102 includes a base arm 104 and a moving arm 106 and, a pair of retractor blades 108 having a side loading blade 110 and a top loading blade 112. The base arm 104 includes a track base 118 and a side loading connector 116 that connects the side loading blade 110. The side loading connector 116 is connected to the track base 118 by a pivot link 117 having two pivots 119 such that the base arm comprises a double hinge. A first track 114 extends perpendicularly from the track base 118 of the base arm 104, the first track 114 including a row of teeth 120. The moving arm 106 is located opposite to the base arm 104. The moving arm 106 includes a first track receptacle 122 and a top loading connector 124 that connects the top loading blade 112. The top loading connector 124 is connected to the track receptacle 122 by a pivot link 126 having two pivots 128 such that the moving arm comprises a double hinge. The moving arm 106 may be advanced along the first track 114 by means of a knob 130 to move the moving arm 106 away from the base arm 104. The moving arm 106 also includes an articulating arm post 132 which provides a connection point for rigidly attaching the first retractor 102 to the surgical table (or other stationary object) with a locking articulating arm.

In surgical use, according to a preferred example, the base arm 104 and the side loading connector 116 are positioned medially (away from the surgeon) and against the esophagus and trachea. The moving arm 106 and the top loading connector 124 is positioned laterally (closest to the surgeon). Hence, the side loading blade 110 and the top loading blade 112 may also be referred to as medial blade and lateral blade, respectively. The retractor 102 may be then used to retract the tissue in a medial-lateral orientation.

Figure 2:
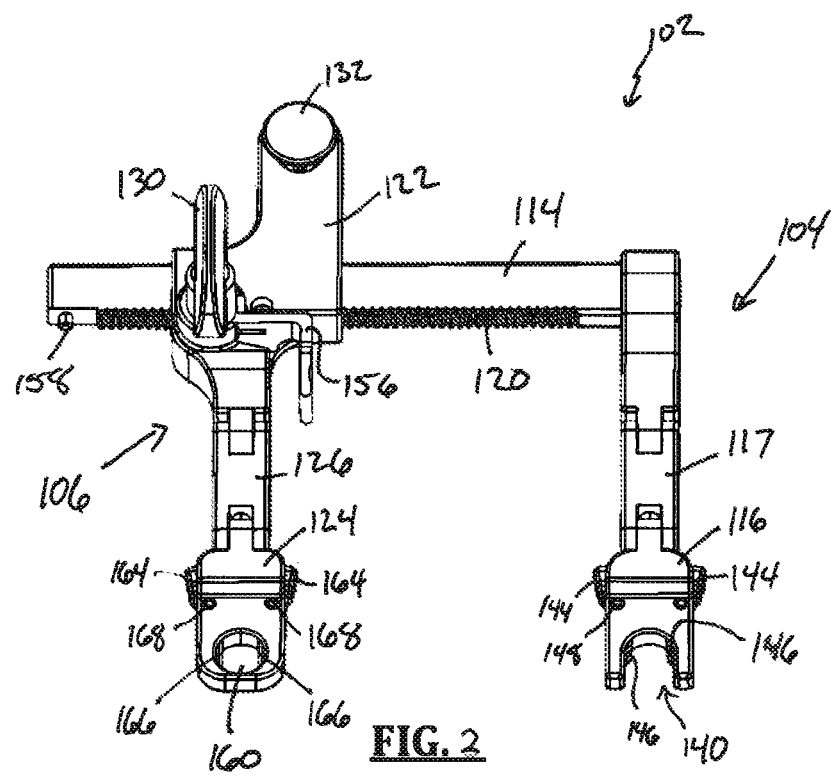
FIG. 2 is a perspective view of the cervical retractor of FIG. 1 without the retractor blades engaged.
Figure 3:
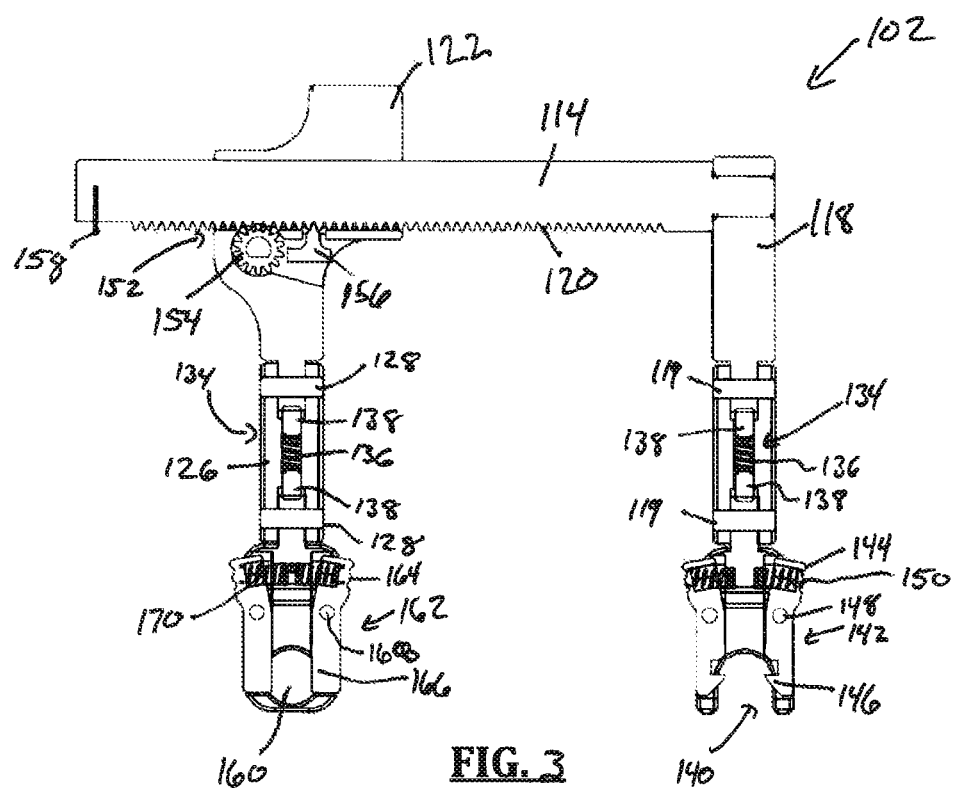
FIG. 3 is a cross section view of the cervical retractor of FIG. 2.

The base arm 104 and moving arm 106 are best illustrated in FIGS. 2-3. The side loading connector 116 is connected to the track base 118 by pivot link 117. The pivot link 117 includes a pair of pivots 119 with one pivot 119 located on each end of the pivot link 117 to permit variability in the height of the side loading connector 116 relative to the track base 118 while maintaining the alignment of the side loading connector 116 generally parallel to the track base 118. The pivot link 117 further includes a friction mechanism 134 for preventing the side loading connector 116 and the pivot link 117 from flopping around. The friction mechanism 134 includes a spring 136 with a pair of friction nubs 138 situated at each end. The friction mechanism 134 creates friction between the first pivot link 117 and the side loading connector 116, and between the pivot link 117 and the track base 118. The friction between the pivot link 117 and each of the side loading connector 116 and the track base 118 is such that the application of force (e.g. directly from the user or from contact with the patient or another retractor, etc. . . . ) is required to adjust the position of the side loading connector 116. This way the side loading connector 116 and pivot link 117 will not flop around and create a disturbance when handling the retractor 102 and particularly when trying to position the retractor 102 in the patient.

The side loading connector 116 includes an open receptacle 140 opening in the free end of the connector 116. Situated along each side of the side loading connector 116 are locking arms 142 that each include a release tab 144 at one end and a locking tooth 146 at the opposite end, the release tab 144 and locking tooth 146 being separated by a pivot 148 that pivotally connects the locking arms 142 to the connector 116. Each of the locking arms 142 is spring loaded with a spring 150 that biases the locking tooth 146 into the open receptacle 140 where it engages with connection post of the side loading retractor blade 110 to lock the blade 110 to the connector. To disengage the side loading blade from the side loading connector 116, the release tabs 144 are depressed which causes the teeth 146 to withdraw into the connector clearing the way for removal of the connection post from the open receptacle 140. A tapered front edge on tooth 146 permit loading of the blade without depressing the release tab 144 to clear the tooth out of the open receptacle 140.

The top loading connector 124 is connected to the track receptacle 122 by pivot link 126. The pivot link 126 includes a pair of pivots 128 with one pivot 128 located on each end of the pivot link 126 to permit variability in the height of the top loading connector 124 relative to the track receptacle 122 while maintaining the alignment of the top loading connector 124 generally parallel to the track receptacle 122. The pivot link 126 further includes a friction mechanism 134 for preventing the top loading connector 124 and the pivot link 126 from flopping around. The friction mechanism 134 includes a spring 136 with a pair of friction nubs 138 situated at each end. The friction mechanism 134 creates friction between the first pivot link 126 and the top loading connector 124, and between the pivot link 126 and the track receptacle 122. The friction between the pivot link 126 and each of the top loading connector 124 and the track receptacle 122 is such that the application of force (e.g. directly from the user or from contact with the patient or another retractor, etc. . . . ) is required to adjust the position of the top loading connector 124. This way the top loading connector 124 and pivot link 126 will not flop around and create a disturbance when handling the retractor 102 and particularly when trying to position the retractor 102 in the patient.

The track receptacle 122 has a passage 152 through which the track 114 passes and which permits the moving arm 106 to translate along the track 114. The moving arm 106 is advanced towards or away from the base arm 104 by turning the knob 130. A gear 154 on the knob 130 extends into track receptacle passage 152 and engages the teeth 120 such that rotation of the knob 130 translates the moving arm 106 along the track either towards or away from the base arm 104, depending on the direction of rotation. The movement of the moving arm 106 towards the base arm 104 is prevented by a lock 156 that engages the track teeth 120 in such a way that motion away from the base arm 106 is permitted while motion towards the base arm is inhibited. By way of example, the lock 156 may be a spring biased pawl pivotally coupled to the track receptacle. The knob 130 may preferably include a friction mechanism to prevent the knob 126 from flopping around. For example, the friction mechanism (not shown) may be similar to the friction mechanism 134 that includes a spring biased friction nub in contact with a hinged portion of the knob. A protrusion 158 on the end of the track 114 prohibits the track receptacle 122 from disengaging from the track 114.

The top loading connector 124 includes a closed receptacle 160 enclosed by the connector 124. Situated along each side of the top loading connector 124 are locking arms 162 that each include a release tab 164 at one end and a locking wedge 166 at the opposite end, the release tab 164 and locking wedge 166 being separated by a pivot 168 that pivotally connects the locking arms 162 to the connector 124. Each of the locking arms 162 is spring loaded with a spring 168 that biases the locking wedge 166 into the closed receptacle 160 where it engages with connection post of the top loading retractor blade 112 to lock the blade 112 to the connector 124. To disengage the top loading blade from the top loading connector 124, the release tabs 164 are depressed which causes the wedges 166 to withdraw into the connector, clearing the way for removal of the connection post from the closed receptacle 160. An upward tapering bottom surface of the locking wedges 166 permit loading of the blade without depressing the release tab 166 to clear the locking wedges from the closed receptacle 160.

FIGS. 4-6 depict the side loading blade 110. The side loading blade 110 includes a blade portion 171 and a connection post 182. The blade portion 171 includes an interior face 172 that faces the operative corridor, an exterior face 174 that faces and engages the body tissue adjacent the operative corridor, a ledge 176 that extends transversely away from the exterior face 174 at a proximal end 177 of the blade portion, and a distal end 178. The interior face 172 includes a shim track 180 that slidably couple a shim and or lighting elements (not shown). The side loading blade 110 may also include at least one suction channel 200 having a suction receptacle 202 and a suction outlet 204. The at least one suction channel 200 is designed to receive and hold a suction instrument within the operative corridor. The distal end 178 may have any number of suitable configurations, including blunt or toothed. The distal end 178 may also be angled away from the interior.

The connection post 182 is coupled to the ledge 176 and serves as an attachment structure for coupling the side loading blade 110 to the side loading connector 116. The connection post 180 includes an upper tier 184, a lower tier 186, an inner post 188, an outer post 190 and a friction element 192. The connection post 182 is designed to provide limited rotation relative to the blade portion 171 such that the side loading blade 110 is configured to self align during retraction to reduce pressure points on retracted tissue. The inner post 188 and the outer post 190 of the connection post 182 are connected by an attachment pin 194. The inner post 188 further includes a slot 196 to allow the attachment pin 194 to pass through. The slot 196 receives the attachment pin 194 and allows the outer post 190 and the attachment pin 194 to rotate. The width of the slot 196 is made larger than the width of the attachment pin 194 so as to allow the attachment pin 194 to move freely in the slot 196. The friction element 162 helps to control rotation of the inner post 188 within the outer post 190. The friction element 192 may be an o-ring. The inner post 188 is fixed to the blade portion 171 with a first connection post set screw 198. Having both the upper tier 184 and the lower tier 186 allows the side loading blade 110 to be connected to two instruments simultaneously. For example, the blade may be inserted through a skin incision while connected to a manual insertion handle. Then the connection post 182 may be coupled to the side loading connector 124 prior to removing the manual handle such that retraction is not lost while engaging the blade 110 and connector 124. Alternatively, the blade 110 may be connected directly to an articulating arm (instead of being attached to retractor 102) while it is connected to a manual insertion handle.

With reference to FIGS. 7-9 the top loading blade 112 is depicted. The top loading blade 112 includes a blade portion 171 and a connection post 208. The blade portion 171 is the same as blade portion 171 of the side loading retractor blade 110. For example, the blade portion includes interior face 172 that faces the operative corridor, an exterior face 174 that faces and engages the body tissue adjacent the operative corridor, a ledge 176 that extends transversely away from the exterior face 174 at a proximal end 177 of the blade portion, and a distal end 178. The interior face 172 includes a shim track 180 that slidably couple a shim and or lighting elements (not shown). The blade portion 171 of top loading blade 112 may also include at least one suction channel 200 having a suction receptacle 202 and a suction outlet 204. The at least one suction channel 200 is designed to receive and hold a suction instrument within the operative corridor. The distal end 178 may have any number of suitable configurations, including blunt or toothed. The distal end 178 may also be angled away from the interior. The top loading blade 112 differs from the side loading blade 110 in the connection post 208 that is connected to the blade portion 171.

The top loading connection post 208 is coupled to the ledge 176 and serves as an attachment structure for coupling the top loading blade 112 to the top loading connector 124. The connection post 208 includes an upper tier 210 and a lower tier 212. The connection post 208 permits rotation of the top loading blade 112 such that the top loading blade 112 self aligns and reduces pressure points on the retracted tissue. Unlike the side loading connector post 182, which rotates (about a limited range) relative to the blade portion 171, the top loading connection post 208 is fixed (via set screw 214) relative to the blade portion 176. Instead, the connection between the upper tier 210 of the connection post 208 and the top loading connector 124 provides for the rotation. Specifically, side grooves 216 formed in the upper tier 210 receive the locking wedges 166. The depth of the side grooves 216 provide for space between the wedges 166 and the inner walls of the grooves 166 which allows rotation (about a limited range) of the top loading blade 112 relative to the top loading connector 124. Having the upper tier 210 and the lower tier 212 allows the top loading blade 112 to be connected to two instruments simultaneously. For example, the blade 112 may be inserted through a skin incision while a manual insertion handle is connected to the lower tier 212. With the manual handle still connected to the lower tier 212, the top loading connector may be attached to the upper tier 210 of the connection post 208 such that retraction is not lost while engaging the blade 110 and connector 124. Alternatively, the blade 112 may be connected directly to an articulating arm (instead of being attached to retractor 102) while it is connected to a manual insertion handle.

Figure 10:
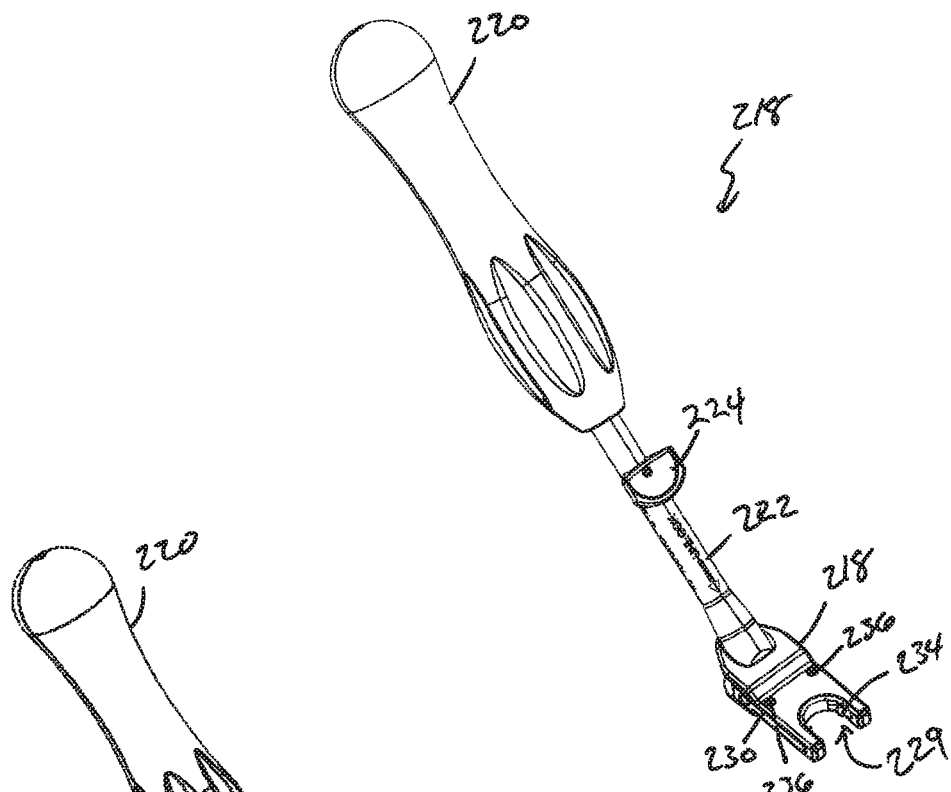
FIG. 10 a perspective view of an insertion handle for use with the side loading retractor blade of FIGS. 4-6 and the top loading retractor blade of FIGS. 7-9, according to one example embodiment.
Figure 11:
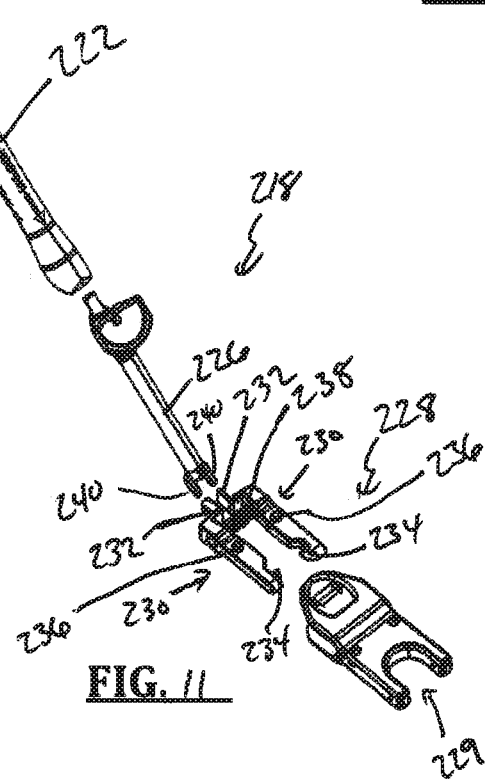
FIG. 11 is an exploded view of the insertion handle of FIG. 10.

FIGS. 10-11 illustrate an insertion handle 218 for advancing the side loading blade 110 and the top loading blade 112 to cervical target site. The insertion handle 218 comprises a grip 220, an outer shaft 222, a lever 224, an inner shaft 226 and an engagement head 228. The engagement head 228 further comprises an open receptacle 229 and a pair of locking arms 230 situated along each side of the side engagement head. Each locking arm 230 includes a tapered engagement extension 232 at one end and a locking tooth 234 at the opposite end, the engagement extension 232 and locking tooth 234 being separated by a pivot 236 that pivotally connects the locking arms 230 to the engagement head 228. The locking arms 230 are spring loaded with a spring 238 that biases the locking teeth 234 into the open receptacle 140 where it engages with either the side loading connection post 182 or the top loading connection post 208. On the side loading blade 110, the insertion handle 218 can connect to either the lower tier 186 or the upper tier 184 of the connection post 182. On the top loading blade 112, the insertion handle 218 can connect to the lower tier 212. A tapered front edge on teeth 234 permit loading of the blade without clearing the teeth 234 out of the open receptacle 229. To withdraw the teeth 234 from the open receptacle and disengage the retractor blade, the lever 22 is depressed. The lever 224 is attached to the inner shaft 226 such that depressing the lever causes the inner shaft 226 to translate towards the engagement head 228. Engagement prongs 240 on the distal end of the inner shaft 226 contact the engagement extensions 232 of the locking arms and force them to move towards each other. The locking arms 230 thus rotate about the pivot 236 and the locking teeth are withdrawn out of the open receptacle 290, freeing the blade 110 or 112.

Figure 12:
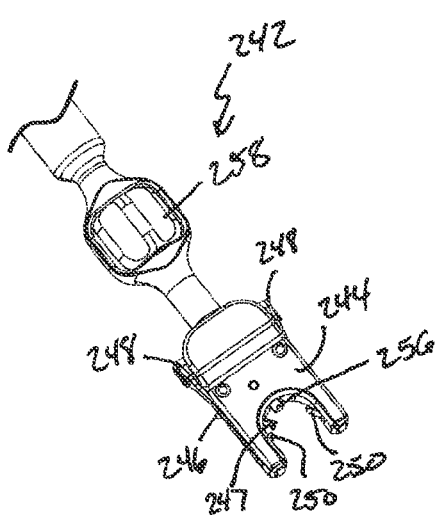
FIG. 12 is a perspective view of an articulating arm connector for securing the retractor relative to the surgical table or other stationary object with an articulating arm, according to one example embodiment.
Figure 13:
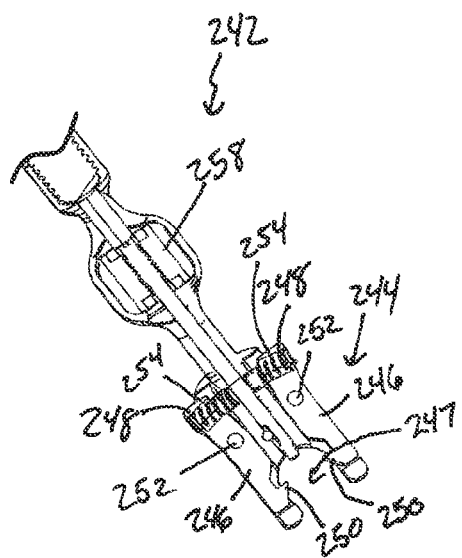
FIG. 13 is an exploded view of the articulating arm connector of FIG. 12.

FIGS. 12-13 illustrate an articulating arm connector 242 for attachment to an articulating arm post 132 of the cervical retractor 102. The articulating arm connector 242 attaches to a free end of the articulating arm (not shown) which may be secured at the opposite end to the surgical table or other stationary object, thus securing the position of the retractor 102 relative to the table. The articulating arm connector 242 includes an engagement head 244 with an open receptacle 247 opening in the free end of the c engagement head 244. Situated along each side of the engagement head 244 are locking arms 246 that each include a release tab 248 at one end and a locking tooth 250 at the opposite end, the release tab 248 and locking tooth 250 being separated by a pivot 252 that pivotally connects the locking arms 246 to the engagement head 244. Each of the locking arms 246 is spring loaded with a spring 254 that biases the locking tooth 250 into the open receptacle 247 where it engages with articulating arm post 132 to lock the retractor 102 to the articulating arm. The articulating arm connector also includes a translating post 256 which is threadedly coupled to a thumbwheel 258. The translating post 256 can be actuated to advance into the open receptacle 256 where it presses against the articulating arm post 132 to provide for a sturdier connection. To disengage the articulating arm connector 242, the release tabs 248 are depressed which causes the teeth 250 to withdraw into the engagement head clearing the way for removal of the articulating arm post 132 from the open receptacle 247. A tapered front edge on teeth 250 permit initial loading of the articulating arm post 132 without depressing the release tab 248 to clear the teeth out of the open receptacle 247.

According to one example, a method of creating an operative corridor to a cervical target site with the retractor 102 is initiated by attaching the side loading blade 110 to the insertion handle 218 via one tier (184, 186) of the first connection post 182. The side loading blade 110 is then retracted into the desired position with the insertion handle and then the blade 110 is locked in place with the articulating arm. To do so the articulating arm connector 242 is connected to the free tier (i.e. the tier that is not connected to the insertion handle 218) of the connection post 182. The articulating arm is then locked, fixing the position of the side loading blade 110. The insertion handle 218 is then removed to free a tier of the connection post 182 and the side loading connector 116 of the retractor body 102 is then attached to the free tier. The top loading blade 112 is then attached to the insertion handle 218 by connecting the insertion handle 218 to the lower tier 212 of the connection post 208. The top loading blade 112 is manually retracted into the desired position and then the top loading connector 124 is attached to the upper tier 210 of the connection post 208. The insertion handle 218 is removed from the lower tier 212. The retractor 100 may then be utilized to retract tissue, for example in a medial-lateral orientation.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An anterior cervical retractor for application to an anterior part of a cervical spine, comprising:
    a retractor body, said retractor body comprising:
        a base arm including a track base, a side loading blade connector coupled to a distal end of said track base, and a track extending perpendicularly from a proximal end of said track base, said track including gear teeth said side loading blade connector including a first top surface, a first bottom surface, a first rear end coupled to said track base, a first front end, and first opposing sides, said side loading blade connector having an open receptacle that extends through the first top and first bottom surfaces and opens in the first front end of the side loading blade connector, said side loading blade connector further including a first pair of locking arms, each of the locking arms of the first pair of locking arms including a release tab and a locking tooth;
        a moving arm including a track receptacle and a top loading blade connector coupled to a distal end of said track receptacle, said track receptacle configured to receive said track therethrough, said moving arm advanceable along said track by rotation of a knob extending from said base arm, said knob connected to a gear that extends into said track receptacle and engages said gear teeth, said top loading blade connector including a second top surface, a second bottom surface, a second rear end coupled to said track receptacle, a second front end, and second opposing sides, said top loading blade connector having a closed receptacle that extends through the second top and second bottom surfaces and is enclosed by the second front end, second rear end, and second opposing sides, said top loading blade connector further including a second pair of locking arms, each of the locking arms of the second pair of locking arms including a second release tab and a tapered wedge;
    a pair of retractor blades, said pair of retractor blades comprising:
        a side loading blade attachable to said side loading blade connector, said side loading blade including a first blade portion and a first connection post, said first blade portion having a first interior face, a first exterior face and a first distal end, said side loading blade configured to attach to the side loading blade connector by advancing said first connection post into said open receptacle through said opening in said first front end of said side loading blade connector, and wherein the first blade portion is rotatable about a limited range relative to at least a portion of the first connection post such that the first blade portion is rotatable about a limited range relative to the base arm when said side loading blade is attached to said side loading blade connector; and
        a top loading blade attachable to said top loading blade connector, said top loading blade including a second blade portion and a second connection post, said second blade portion having a second interior face, a second exterior face and a second distal end, said top loading blade configured to attach to the top loading blade connector by advancing said second connection post into said closed receptacle in a direction such that the second connection post enters the closed receptacle from the second bottom surface, wherein said second connection post is fixed relative to said second blade portion and said second connection post is rotatable about a limited range relative to the top loading blade connector such that the second blade portion is rotatable about a limited range relative to the moving arm when said top loading blade is attached to said top loading blade connector.

2. The anterior cervical retractor of claim 1, wherein each of said locking arms of said first pair of locking arms is biased such that the respective locking tooth extends into the open receptacle to capture said first connection post of said side loading blade in said open receptacle.

3. The anterior cervical retractor of claim 2, wherein operating said release tabs of said first pair of locking arms disengages each locking tooth from the first connection post to remove the side loading blade from the side loading blade connector.

4. The anterior cervical retractor of claim 3, wherein each of said locking arms of said second pair of locking arms is biased such that the respective tapered wedge extends into the closed receptacle to capture said second connection post of said top loading blade in said closed receptacle and wherein operating said second release tabs of said second pair of locking arms disengages each tapered wedge from said second connection post to remove said top loading blade from said top loading blade connector.

5. The anterior cervical retractor of claim 1, wherein said side loading blade connector is coupled to said track base via a first pivot piece, the first pivot piece being pivotally coupled at one end to the side loading blade connector and being pivotally coupled at an opposite end to the track base such that a height of said side loading blade connector is adjustable relative to said track base while maintaining an alignment of said side loading blade connector parallel to said track base, said first pivot piece further including a first friction mechanism for preventing said side loading blade connector and said first pivot piece from flopping around.

6. The anterior cervical retractor of claim 5, wherein said first friction mechanism includes a first spring and a pair of first friction nubs, each of the pair of first friction nubs situated at an opposite end of the first spring, and wherein one of said first friction nubs creates friction between said first pivot piece and said side loading blade connector and the other of said first friction nubs creates friction between said first pivot piece and said track base.

7. The anterior cervical retractor of claim 1, wherein said top loading blade connector is coupled to said track receptacle via a second pivot piece, said second pivot piece being pivotally coupled at one end to the top loading blade connector and being pivotally coupled at an opposite end to the track receptacle such that a height of said top loading blade connector is adjustable relative to said track receptacle while maintaining alignment of said top loading blade connector parallel to said track receptacle, said second pivot piece further including a second friction mechanism for preventing said top loading blade connector and said second pivot piece from flopping around.

8. The anterior cervical retractor of claim 7, wherein said second friction mechanism includes a second spring and a pair of second friction nubs, each of the pair of second friction nubs situated at an opposite end of the second spring, and wherein one of said second friction nubs creates friction between said second pivot piece and said top loading blade connector and the other of said second friction nubs creates friction between said second pivot piece and said track receptacle.

9. The anterior cervical retractor of claim 1, wherein at least one of said side loading blade and said top loading blade includes a suction channel designed to receive and maintain a suction instrument within said retractor.

10. The anterior cervical retractor of claim 1, wherein said rotation of the first blade portion about the limited range relative to the base arm and rotation of the second blade portion about the limited range relative to the moving arm facilitates self-alignment of the side loading and top loading blades to reduce pressure points on retracted tissue.

11. The anterior cervical retractor of claim 1, wherein said first connection post includes an upper tier and a lower tier such that said side loading blade is attachable to two instruments simultaneously.

12. The anterior cervical retractor of claim 11, wherein said second connection post includes an upper tier and a lower tier such that said top loading blade is attachable to two instruments simultaneously.

13. The anterior cervical retractor of claim 11, wherein one of said instruments is an insertion handle and a second of said instruments is the retractor body.

14. The anterior cervical retractor of claim 1, wherein said first distal end of said first blade portion is one of blunt and toothed.

15. The anterior cervical retractor of claim 1, wherein said second distal end of said second blade portion is one of blunt and toothed.

16. The anterior cervical retractor of claim 1, wherein the track receptacle includes an articulating arm post for rigid connection of the retractor body to a stationary object.

* * * * *